United States Patent [19]

Ogata et al.

[11] 4,272,382

[45] Jun. 9, 1981

[54] PROCESS FOR SEPARATING CYCLIC PHOSPHAZENE OLIGOMERS

[75] Inventors: Yuzuru Ogata, Tokushima; Yoshifumi Nakacho, Sakai, both of Japan

[73] Assignee: Otsuka Chemical Co. Ltd., Osaka, Japan

[21] Appl. No.: 97,893

[22] Filed: Nov. 27, 1979

[30] Foreign Application Priority Data

Apr. 7, 1979 [JP] Japan ................................ 54-42191

[51] Int. Cl.³ .............................................. B01D 15/00
[52] U.S. Cl. .................................. 210/660; 210/690; 423/300; 423/302
[58] Field of Search ............................ 210/24, 39–41, 210/660, 690; 423/300, 302; 528/399

[56] References Cited

U.S. PATENT DOCUMENTS

| 3,694,171 | 9/1972 | Dreifus | 423/302 |
| 3,702,833 | 11/1972 | Rose et al. | 423/302 |
| 3,869,540 | 3/1975 | Hardy | 423/302 |

*Primary Examiner*—Ivars C. Cintins
*Attorney, Agent, or Firm*—Armstrong, Nikaido, Marmelstein & Kubovcik

[57] ABSTRACT

A process for separating cyclic phosphazene oligomers from a mixture containing cyclic phosphazene oligomers and linear phosphazenes by bringing the mixture into contact with a mineral adsorbent composed of mainly silicon and/or aluminum and removing the adsorbent. Cyclic phosphazene oligomers of high purity can be readily separated in high yields by the process.

3 Claims, No Drawings

PROCESS FOR SEPARATING CYCLIC PHOSPHAZENE OLIGOMERS

BACKGROUND OF THE INVENTION

The present invention relates to a process for separating cyclic phosphazene oligomers, and more particularly to a process for separating cyclic phosphazene oligomers from a mixture containing cyclic phosphazene oligomers and linear phosphazenes by treating the mixture with a mineral adsorbent, by which cyclic phosphazene oligomers of high purity can be readily separated in high yields.

The term "linear phosphazenes" as used herein means linear halogenophosphonitriles usually having a degree of polymerization of 2 to 50,000, and the term "cyclic phosphazene oligomers" as used herein means cyclic halogenophosphonitriles usually having a degree of polymerization of 3 to 20.

In the early part of the 19th century, it was found that hexachlorocyclotriphosphonitrile (hereinafter referred to as "trimer") was produced by the reaction of phosphorus pentachloride and ammonia or ammonium chloride, and since then, researches had been variously made to develop a use for the cyclic trimer, but the cyclic trimer had not been put into practical use till the mid-1960s. In the mid-1960s, there was reported a process for preparing a high polymer (i.e. polychlorophosphonitrile, hereinafter referred to as "phosphazene polymer") which is soluble in organic solvents by ring-opening polymerization of the cyclic trimer, and it was also found that polymeric materials having characteristics that conventional polymeric materials did not possess could be obtained by substituting various nucleophilic substituent groups for chlorine atom bonding to phosphorus atom constituting the skeleton of the phosphazene polymer molecule.

Because of the properties as inorganic material, there have been extensively made researches for applications of the phosphazene polymers to the industrial and medical fields such as fireproofing foamed rubbers, flame retarders for plastics, O-rings, gaskets, hoses for hydrocarbon fuels, substitute blood vessels and artificial internal organs. With the increase of the use of the phosphazene polymers, the demand for cyclic phosphazene oligomers, particularly the cyclic trimer has increased, and on the other side, there have been proposed various processes for the preparation of the cyclic phosphazene oligomers.

The reaction of phosphorus pentachloride or an organic group-substituted phosphorus chloride with ammonia or ammonium chloride is a popular process for the preparation of cyclic phosphazene oligomers $(PNCl_2)_n$ wherein n is an integer of 3 or more. For instance, the cyclic trimer is generally prepared as follows: Phosphorus pentachloride and a slight excess of ammonium chloride are reacted in a halogenated organic solvent such as symtetrachloroethane or chlorobenzene in the absence or presence of a catalyst under reflux. Since linear phosphazenes are necessarily by-produced, after thoroughly releasing the generated hydrochloric acid from the reaction system cyclic phosphazene oligomers are then separated from the linear phosphazenes by distilling away the solvent and subjecting the residue to extraction with a solvent capable of dissolving the cyclic phosphazene oligomers but not dissolving the linear phosphazenes, e.g. petroleum ether or hexane. The cyclic trimer is recovered from the obtained cyclic phosphazene oligomers by a post-treatment such as a distillation, sublimation or recrystallization method.

However, there are some problems in such a preparation of cyclic phosphazene oligomers. As stated above, the by-production of the linear phosphazenes is unavoidable, and it is necessary to separate the cyclic phosphazene oligomers from the linear phosphazenes. However, since there is no appropriate extraction solvent which is incompatible with reaction solvents, the separation must be conducted by troublesome distillation-extraction procedures. Moreover, in order to conduct complete separation, the reaction solvent must be completely distilled away, and upon the distillation the cyclic trimer and octachlorocyclotetraphosphonitrile (hereinafter referred to as "tetramer") are liable to be lost. Also, a large quantity of an extraction solvent is required to conduct satisfactory extraction. Even if such a troublesome separation procedure is conducted, complete extraction is impossible and the extraction ratio of the cyclic phosphazene oligomers from the reaction product is at most 90% by weight. Also, some incorporation of linear phosphazenes into the extract is unavoidable. It is general practice to recover the cyclic trimer from the extracted cyclic phosphazene oligomers by a distillation, sublimation or recrystallization method, but the incorporation of the linear phosphazenes, even in a trace amount, tends to cause gelation of the cyclic phosphazene oligomers during the above recovering procedure such as distillation and the yield of the cyclic trimer is remarkably decreased.

When a catalyst, e.g. a metal or a metal salt is employed in the reaction, a part of the metal or metal salt catalyst may form adducts with linear phosphazenes and also with cyclic phosphazene oligomers, especially with the cyclic phosphazene oligomers of more than decachlorocyclopentaphosphonitrile (hereinafter referred to as "pentamer"), and these adducts often cause gelation upon recovering the cyclic trimer. Since the adducts cannot be separated by the extraction separation, this is also a problem to be solved.

A wet process using a solvent and a dry process using no solvent are known as the process for preparing cyclic phosphazene oligomers. Since the former can usually produce the cyclic phosphazene oligomers in higher yields than the latter, attempts for industrialization have been made in general by a wet process. When the recovered solvent is reused, however, the yields of the cyclic phosphazene oligomers are remarkably lowered. Therefore, purification of the recovered solvent is necessary and this increases the production cost.

SUMMARY OF THE INVENTION

In accordance with the present invention, there is provided a process for separating cyclic phosphazene oligomers which comprises bringing a mixture containing cyclic phosphazene oligomers and linear phosphazenes into contact with a mineral adsorbent and removing said adsorbent.

Cyclic phosphazene oligomers of high purity can be readily separated in high yields by the process of the present invention.

DETAILED DESCRIPTION

The process of the present invention can selectively separate cyclic phosphazene oligomers from a mixture of cyclic phosphazene oligomers and linear phosphazenes, and is particularly suited for recovering only the cyclic phosphazene oligomers from reaction mixtures which are obtained in various known processes for the preparation of cyclic phosphazene oligomers. The reaction mixture usually contains cyclic phosphazene oligomers, by-produced linear phosphazenes, unreacted materials and other by-products, and further a catalyst when it is used, and in general, the degree of polymerization of the cyclic phosphazene oligomers falls within the range of 3 to 20 and the degree of polymerization of the linear phosphazenes falls within the range of 2 to 50,000. According to the present invention, the cyclic phosphazene oligomers of high purity can be readily separated in high yields, since the linear phosphazenes and the other impurities contained in the reaction mixture are adsorbed and removed by a mineral adsorbent. Also, since the separated cyclic phosphazene oligomers contain substantially no linear phosphazenes, the gelation of the cyclic phosphazene oligomers is avoided in the recovery of a specific cyclic phosphazene oligomer from the separated cyclic oligomers, and in case that the preparation is conducted by a wet process using a solvent, the solvent can be recovered without any loss and can be reused as it is without lowering the yield of the cyclic phosphazene oligomers.

The process of the present invention is applicable to a mixture of cyclic and linear halogenophosphonitriles or organic group-substituted halogenophosphonitriles such as phenylhalogenophosphonitriles, ethylhalogenophosphonitriles and iso-propylhalogenophosphonitriles.

There are known various processes for preparing cyclic phosphazene oligomers such as cyclic chlorophosphazene, bromophosphazene or other halogenophosphazene oligomers and cyclic organic group-substituted chlorophosphazene, bromophosphazene or other halogenophosphazene oligomers. The process of the present invention is availably employed to separate the cyclic phosphazene oligomers from the reaction mixtures obtained in such processes, for instance, the reaction mixtures obtained by the reactions of $P+X_2+NH_3$ or $NH_4X$, $P+X_2+NH_3+HX$, $PX_3+X_2+NH_3$ or $NH_4X$, $PX_3+X_2+NH_3+HX$, $PX_5+NH_3$ or $NH_4X$, $PX_5+NH_3+HX$, $RPX_2+X_a+NH_4X$, $RPX_4+NH_4X$, $R_2PX+X_2+NH_4X$, and $R_2PX_3+NH_4X$, wherein X is a halogen and R is phenyl, ethyl or iso-propyl group. These reactions are carried out in the presence or absence of a solvent and of a catalyst such as a metal, a metal salt, a metal complex, phosphoryl chloride or thiophosphoryl trichloride.

Adsorbents composed of silicon and/or aluminum as a main component are employed as a mineral adsorbent in the present invention. Examples of the mineral adsorbent employed in the present invention are vermiculite, sericite, talc, mica, diatomaceous earth, kaolin, bentonite, montmorillonite, acid clay, activated clay, silica, alumina, zeolite, synthetic zeolite and molecular sieves (commercially available under the trade name "Molecular Sieves" made by Linde Company in U.S.A.). Some of the mineral adsorbents always have crystallization water or adsorption water at room temperature, but the crystallization water and adsorption water have substantially no effect on the yield of the separation of the cyclic oligomers.

The mineral adsorbent is employed in an amount of 0.5 to 10 parts by weight, preferably 1 to 5 parts by weight to one part by weight of the linear polymers contained in a mixture to be treated. When the adsorbent is employed within the above range, the linear phosphazenes and other impurities such as unreacted materials, catalyst and other by-products as contained in reaction mixtures are efficiently adsorbed by the adsorbent, and the cyclic oligomers of high purity are recovered in high yields. The use of the adsorbent in an amount of more than 10 parts by weight does not prevent the separation of the cyclic oligomers, but the post-treatment such as disposal and regeneration of the adsorbent becomes troublesome. When the amount is less than 0.5 parts by weight, removal of the linear phosphazenes is insufficient.

The process of the present invention will be explained below with taking a reaction mixture containing cyclic chlorophosphazene oligomers as an example.

Synthesis of cyclic chlorophosphazene oligomers is generally carried out by heating phosphorus pentachloride or an organic group-substituted phosphorus chloride and ammonia or ammonium chloride in the presence or absence of an appropriate solvent such as benzene, toluene, xylene, chlorobenzene, dichlorobenzene, tetrachloroethane, nitrobenzene or trichlorobenzene and in the presence or absence of a catalyst. In the obtained reaction mixture, linear chlorophosphazenes, unreacted starting materials and a catalyst when it has been used are present in addition to a mixture of the cyclic phosphazene oligomers from the trimer to the eicosamer. In the reaction under ordinary conditions, the cyclic oligomers are produced as a main product, and the proportion of the produced linear phosphazenes is from several % to about 40% by weight. Particularly, when the process of the synthesis is one aiming at producing the cyclic trimer, the proportion of the produced linear phosphazenes is less than 10% by weight. The obtained reaction products assume a brown to black color. The post-treatment by conventional processes often takes much time and labor in decolorization. According to the present invention, colorless cyclic oligomers containing no linear phosphazenes nor other by-products can be almost quantitatively recovered from the reaction mixture. Moreover, when a catalyst has been employed in the synthesis, the catalyst can also be completely removed.

Mineral adsorbent powder is added to a reaction mixture and is treated at a temperature of from room temperature to 200° C., preferably 50° to 150° C. for 10 minutes to 10 hours. After the completion of the treatment, the adsorbent is removed, for instance, by filtration. In case that the reaction mixture to be treated contains no solvent, after the treatment the reaction mixture may be dissolved in a solvent which may be those used in the synthesis by a wet process, followed by the removal of the adsorbent by filtration. The treatment at a temperature of more than 200° C. may be conducted. However, in case of treating the reaction mixture in a solvent system, a solvent having a boiling point of higher than 200° C. must be employed, and in case of treating the reaction mixture in a non-solvent system, a special apparatus is required in the treatment because the boiling points of the cyclic trimer and tetramer are lower than 200° C. When the treating temperature is less than room temperature, very long time, e.g. over 24 hours is required in the treatment and moreover the efficiency is lowered.

Thus, the present invention produces excellent effects that the post-treatment after the preparation of cyclic phosphazene oligomers can be simplified and the recovery percent and purity of the cyclic oligomers can be remarkably increased. Also, the present invention is very useful for not only the separation of the cyclic oligomers, but also the purification of the cyclic oligomers.

The present invention will be more particularly described and explained by means of the following Examples, in which all % are by weight.

EXAMPLE 1

A 200 ml. flask was charged with 50 g. of a mixture of 60% of cyclic trimer of chlorophosphazene, 20% of cyclic tetramer of chlorophosphazene and 20% of linear phosphazenes. To the flask was added 10 g. of activated clay, and the mixture was treated for 1 hour with agitation of an oil bath at 140° C. The flask was then taken out of the oil bath, and the mixture was dissolved in monochlorobenzene and filtered to remove the activated clay. Monochlorobenzene was distilled away under reduced pressure to give 39.5 g. of a white crystal. The obtained crystal was completely soluble in hexane and consisted of 75.9% of the cyclic trimer and 24.1% of the cyclic tetramer. No linear phosphazenes were included in the crystal.

The recovery percents of the trimer and the tetramer were 99.9% and 95.2%, respectively, and they were almost quantitatively recovered.

EXAMPLE 2

A 500 ml. four neck flask was charged with 32.1 g. (0.6 mole) of ammonium chloride, 83.3 g. (0.4 mole) of phosphorus pentachloride, 0.4 g. of zinc chloride and 200 ml. of monochlorobenzene, and the reaction was carried out for 5 hours under reflux of monochlorobenzene, during which hydrochloric acid was nearly generated and released outside the reaction system. It was determined that the reaction mixture contained 23.1 g. of trimeric cyclic chlorophosphazene and 5 g. of tetrameric cyclic chlorophosphazene by gas chromatography.

To the thus obtained reaction mixture was added 15 g. of activated clay, and was refluxed for 1 hour. After there fluxing, precipitate was removed by filtration and the filtrate was concentrated to give 38.5 g. of a light yellow solid. The solid was completely soluble in any of n-hexane and petroleum ether, and contained no linear phosphazenes. Also, no zinc was detected by atomic absorption analysis. It was determined by gas chromatography that 22.8 g. of the cyclic trimer and 4.8 g. of the cyclic tetramer were contained in the recovered solid cyclic chlorophosphazene oligomers. The recovery percents of the trimer and tetramer were 98.7% and 96.0%, respectively.

As comparison, the preparation of phosphazene oligomers was conducted in the same manner as the above, and the separation procedure of the obtained reaction mixture was conducted according to a conventional process in which the monochlorobenzene used as the reaction solvent was completely distilled away from the reaction mixture, and the residue was then extracted with n-hexane to recover the cyclic oligomers. However, the recovered product contained not only 33.9 g. of the cyclic oligomers (cyclic trimer: 20.2 g., cyclic tetramer: 3.8 g.), but also 6.5 g. of the linear phosphazenes. Moreover, the cyclic oligomers contained 500 p.p.m. of zinc.

The above results show that according to the present invention, the linear phosphazenes, catalyst and unreacted materials are completely removed and the cyclic oligomers of high purity can be recovered in high yields.

EXAMPLES 3 to 6

The procedures of Example 2 were repeated except that a mineral adsorbent as shown in the following Table was employed instead of activated clay.

The results are shown in the Table.

| Ex. No. | Adsorbent | Recovery of cyclic oligomers*1 Trimer % | Recovery of cyclic oligomers*1 Tetramer % | Content of Zn in recovered cyclic oligomers*2 p.p.m. | Content of linear phosphazenes in recovered cyclic oligomers % |
|---|---|---|---|---|---|
| 3 | Silica | 95.0 | 92.0 | 0 | 0 |
| 4 | Diatomaceous earth | 98.2 | 95.8 | 0 | 0 |
| 5 | Molecular Sieves | 95.8 | 92.2 | 0 | 0 |
| 6 | Synthetic zeolite | 97.0 | 96.5 | 0 | 0 |
| Com. Ex.*3 | — | 87.4 | 76.0 | 500 | about 1 |

(Note)
*1Recovery of cyclic oligomers shows percent of the trimer or tetramer in the recovered cyclic oligomers to the trimer or tetramer in the reaction mixture, determined by a gas chromatography.
*2Content of Zn shows values determined by atomic absorption analysis.
*3Comparative Example was carried out as follows: The cyclic trimer and tetramer contained in the obtained reaction mixture were determined by a gas chromatography. After removing the unreacted ammonium chloride by filtration, the resulting filtrate was concentrated to dryness and the residue was extracted with n-hexane to recover the cyclic oligomers. The cyclic trimer and tetramer in the recovered cyclic oligomers were determined by a gas chromatography.

What we claim is:

1. A process for separating cyclic phosphazene oligomers which comprises adding a mineral adsorbent to a mixture containing cyclic phosphazene oligomers and linear phosphazenes, the amount of said mineral adsorbent being 0.5 to 10 parts by weight to 1 part by weight of the linear phosphazenes in the mixture and said mineral adsorbent being at least one mineral selected from the group consisting of vermiculite, sericite, talc, mica, diatomaceous earth, kaolin, bentonite, montmorillonite, acid clay, activated clay, silica, alumina, zeolite, synthetic zeolite and molecular sieves; maintaining said mineral adsorbent in said mixture for a period of from 10 minutes to 10 hours at a temperature of from room temperature to 200° C.; and thereafter removing said mineral adsorbent from said mixture.

2. The process of claim 1, wherein said mixture is a reaction mixture obtained by a reaction of P, $X_2$ and $NH_3$ or $NH_4X$; P, $X_2$, $NH_3$ and HX; $PX_3$, $X_2$ and $NH_3$ or $NH_4X$; $PX_3$, $X_2$, $NH_3$ and HX; $PX_5$ and $NH_3$ or $NH_4X$; $PX_5$, $NH_3$ and HX; $RPX_2$, $X_2$ and $NH_4X$; $RPX_4$ and $NH_4X$; $R_2PX$, $X_2$ and $NH_4X$; $R_2PX_3$ and $NH_4X$, in which X is a halogen and R is a phenyl, ethyl or iso-propyl group.

3. The process of claim 1, wherein the cyclic phosphazene oligomers contained in said mixture are a member selected from the group consisting of cyclic dihalogenophosphonitrile oligomers, cyclic monophenylmonohalogenophosphonitrile oligomers, cyclic monoethylmonohalogenophosphonitrile oligomers and cyclic monoiso-propylmonohalogenophosphonitrile oligomers.

* * * * *